US00PP12254P2

(12) United States Plant Patent
Osiecki

(10) Patent No.: US PP12,254 P2
(45) Date of Patent: Dec. 4, 2001

(54) ANTHURIUM PLANT NAMED 'AEIGHTEEN'

(75) Inventor: Marian W. Osiecki, Marianna, FL (US)

(73) Assignee: Oglesby Plants Intl., Inc., Altha, FL (US)

( * ) Notice: Subject to any disclaimer, the term of this patent is extended or adjusted under 35 U.S.C. 154(b) by 0 days.

(21) Appl. No.: 09/405,606

(22) Filed: Sep. 24, 1999

(51) Int. Cl.[7] ..... A01H 5/00

(52) U.S. Cl. ..... Plt./365

(58) Field of Search ..... Plt./365

(56) References Cited

PUBLICATIONS

Webster's II. New Riverside University Dictionary. The Riverside Publishing Company. p. 680, 1994.*

Huxley, A., Griffiths, M., Levy, M. The New Royal Horticultural Society Dictionary of Gardening. The Stockton Press, p. xliii, 1992.*

* cited by examiner

*Primary Examiner*—Gary Benzion
*Assistant Examiner*—Michelle Kizilkaya
(74) *Attorney, Agent, or Firm*—C. A. Whealy

(57) ABSTRACT

A new and distinct cultivar of Anthurium named 'Aeighteen' particularly characterized by its dwarf growth habit; vigor; freely, year-round, and exceptionally early flowering; purple-colored spathes and fairly light-colored spadices; spathes that are held above or at the foliage level on moderately strong peduncles; and very good longevity maintaining lavender color for about five weeks.

2 Drawing Sheets

BACKGROUND OF THE INVENTION

The present invention relates to a new and distinct cultivar of Anthurium plant, botanically known as Anthurium hybrid, and hereinafter referred to by the cultivar name Aeighteen.

The new Anthurium is a product of a planned breeding program conducted by the Inventor in Altha, Fla. The objective of the breeding program was to develop early-flowering dwarf pot Anthuriums with attractive spathe colors.

The new Anthurium originated from a cross made by the Inventor in 1993, of a proprietary seedling selection of Anthurium hybrid code number 91-94-2 as the male, or pollen, parent with the Anthurium hybrid cutlivar A2, disclosed in U.S. Plant Pat. No. 10,210, as the female, or seed, parent. The cultivar Aeighteen was discovered and selected by the Inventor in 1994 as a seedling within the progeny of the stated cross in a controlled environment in Altha, Fla.

Asexual propagation of the new cultivar by tissue culture in Altha, Fla. has shown that the unique features of this new Anthurium plant are stable and reproduced true to type in successive generations.

SUMMARY OF THE INVENTION

The new Anthurium has not been observed under all possible environmental conditions. The phenotype may vary somewhat with variations in environment such as temperature, light intensity, fertilizer rate, irrigation amount and frequency, and/or propagation procedures without, however, any variance in genotype.

The following traits have been repeatedly observed and are determined to be the unique characteristics of 'Aeighteen'. These characteristics in combination distinguish 'Aeighteen' as a new and distinct cultivar:

1. Plants of the new Anthurium have a dwarf growth habit making them suitable for 7.5 to 15-cm containers.

2. Plants of the new Anthurium are vigorous.

3. Plants of the new Anthurium are freely flowering, flower year-round and flower exceptionally early; flowers typically develop on plants about 7 months after planting of tissue culture-produced microcuttings.

4. Plants of the new Anthurium have purple-colored glossy spathes and fairly light-colored spadices.

5. Spathes are held above or at the foliage level on moderately strong peduncles.

6. Spathes of plants of the new Anthurium have very good longevity maintaining lavender color for about five weeks. With subsequent development spathes gradually become green, and retain ornamental value for several months past maturity.

Plants of the new Anthurium are distinguished from plants of the parent cultivar A2 primarily in spathe color as plants of the cultivar A2 have pink-colored spathes. In addition, plants of the new Anthurium differ from plants of the cultivar A2 in the following characteristics:

1. Plants of the new Anthurium are less freely branching and have a more open plant habit than plants of the cultivar A2.

2. Mature leaves of plants of the new Anthurium are darker green and slightly glossier than mature leaves of plants of the cultivar A2.

3. Mature leaves of plants of the new Anthurium are more lanceolate, narrower, longer and more upright than mature leaves of plants of the cultivar A2.

4. Plants of the new Anthurium flower earlier than plants of the cultivar A2.

5. Spathes of plants of the new Anthurium are more ovate, flatter, less puckered, glossier and narrower than spathes of plants of the cultivar A2.

6. Under high light and high temperature conditions, spathe color of plants of the new Anthurium tends to fade earlier than spathe color of plants of the cultivar A2.

7. Peduncles of plants of the new Anthurium are thinner, weaker and usually longer than peduncles of plants of the cultivar A2.

Plants of the new Anthurium are distinguished from plants of its sibling cultivar Atwelve, disclosed in U.S. Plant patent application Ser. No. 09/292,198, primarily in spathe color as plants of the cultivar Atwelve have red-colored spathes. In addition, plants of the new Anthurium differ from plants of the cultivar Atwelve in the following characteristics:

1. Young leaves of plants of the new Anthurium are green in color whereas young leaves of plants of the cultivar Atwelve are between brown and green in color.

2. Mature leaves of plants of the new Anthurium are more lanceolate, narrower, longer and more upright than mature leaves of plants of the cultivar Atwelve.

3. Plants of the new Anthurium flower slightly earlier than plants of the cultivar Atwelve.

4. Spathes of plants of the new Anthurium are more ovate, flatter, less puckered, glossier and narrower than spathes of plants of the cultivar Atwelve.

5. Under high light and high temperature conditions, spathe color of plants of the new Anthurium tends to fade earlier than spathe color of plants of the cultivar Atwelve.

6. Peduncles of plants of the new Anthurium are thinner, weaker and usually longer than peduncles of plants of the cultivar Atwelve.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the first sheet comprises a frontal perspective view of a typical plant of 'Aeighteen' in a 10-cm container about 10.5 months after planting a single tissue culture-produced microcutting.

The photograph at the bottom of the first sheet comprises a close-up view of a typical spathe and spadix.

The photograph at the top of the second sheet comprises a close-up view of the upper surface of a typical fully expanded leaf.

The photograph at the bottom of the second sheet comprises a close-up view of the lower surface of a typical fully expanded leaf. Colors in the photographs may differ slightly from the color values cited in the detailed botanical description which accurately describe the colors of the new Anthurium.

DETAILED BOTANICAL DESCRIPTION

The following observations and measurements were recorded during the summer on plants grown in Apopka, Fla. in polycarbonate-covered greenhouses and under conditions which closely approximate those used in commercial horticultural practice. During the production of these plants, day temperatures ranged from 23 to 28° C., night temperatures ranged from 20 to 23° C., and light level ranged from 800 to 1,500 foot-candles. Plants used for this description were grown as single plants in 10-cm containers and were about 10.5 months from planting a tissue culture-produced microcutting. Older plants differ in some morphological characteristics such as leaf and spathe shape. Fully developed plant structures and organs were used for the following observations and measurements unless otherwise indicated.

In the following description, color references are made to The Royal Horticultural Society Colour Chart except where general terms of ordinary dictionary significance are used. Numerical measurements represent averages from typical plants of 'Aeighteen'.

Botanical classification: Anthurium hybrid cultivar Aeighteen.

Parentage:

*Male, or pollen, parent.*—Proprietary seedling selection of Anthurium hybrid code number 91-94-2.

*Female, or seed, parent.*—Anthurium hybrid cultivar A2, disclosed in U.S. Plant Pat. No. 10,210.

Propagation:

*Type.*—By tissue culture.

*Time to initiate roots.*—Summer: About 21 days at about 25 to 30° C. soil temperature. Winter: About 28 days at about 22 to 27° C. soil temperature.

*Time to produce a rooted liner.*—Summer: About 16 to 18 weeks at about 25 to 30° C. soil temperature. Winter: About 18 to 20 weeks at about 22 to 27° C. soil temperature.

*Root characteristics.*—Thick, fleshy, and freely branching.

Plant description:

*Growth habit.*—Dwarf with a short main stem and few lateral shoots, relatively open plant form; inverted triangle. Appropriate for 7.5 to 15-cm containers.

*Plant size.*—Height, soil surface to top of leaf canopy: About 18.1 cm. Height, soil surface to top of spathes: About 16.6 cm. Diameter (area of spread): About 36.1 cm.

*Plant vigor.*—Vigorous.

*Crop time.*—Plants grown in 10-cm containers begin flowering about seven months after planting tissue culture-produced microcuttings and plants are typically saleable about nine months after planting.

*Leaf blade.*—Shape: Between lanceolate and ovate. Apex: Acuminate, very long. Base: Obtuse with some truncate tendencies, often asymmetrical. Margin: Entire. Length, mature leaves: About 16.1 cm. Width, mature leaves: About 7.3 cm. Length to width ratio, mature leaves: About 2.2 to 1. Aspect: Leaves initially upright, then towards horizontal. Texture: Thick, leathery, smooth. Surface: Slightly glossy, younger leaves more glossy than older leaves. Veins: Prominent near leaf base, less conspicuous near apex. Color: Newly unrolled leaf, upper surface: Darker than 146A. Newly unrolled leaf, lower surface: Between 148A, 147B and 146B. Mature leaf, upper surface: Darker and more green than 147A; veins 144A. Mature leaf, lower surface: Between 147B, 146A and 146B; veins, 144A to 144B or 146B to 146C.

*Petiole.*—Length: About 9.2 cm. Diameter, just below geniculum: About 3.3 mm. Geniculum length: About 1.2 cm. Geniculum diameter: About 4 mm. Petiole wings, length: About 1.6 cm. Petiole wings, width: About 4.5 mm. Color: Newly unrolled leaves, front surface: 146A. Newly unrolled leaves, back surface: 144A. Fully expanded leaves: Geniculum, front surface: 146A. Geniculum, back surface: 144A. Winged area: 146A. Above winged area, front surface: 146A. Above winged area, back surface: 146A.

Inflorescence description:

*Inflorescence arrangement.*—Spathes with spadices held above or just at the foliar plane on moderately strong peduncles. Inflorescences positioned in the center of the plant. Flowering structures arise from leaf axils. Freely flowering; numerous spathes/spadices per plant, about 3.7 inflorescences per plant. Flowering exceptionally early, flowers typically develop on plants about seven momths after planting of tissue culture-produced microcuttings. Flowering continuous and year-round.

*Inflorescence longevity.*—Spathes of plants of the new Anthurium have very good longevity maintaining lavender color for about five weeks following appearance of bud above or among the foliage. With subsequent development spathes gradually become green, and retain ornamental value for several months past maturity. Inflorescences persistent.

*Fragrance.*—Mature inflorescences have a slight fragrance typical of Anthurium.

*Flowers/reproductive organs.*—Quantity per spadix: Numerous, about 7 to 9 flowers per linear centimeter of spadix (mid-section). Pistil: Large in relation to perianth; strongly contrasting with perianth. Stigma small, almost flat. Pistil about 1.5 to 2 mm in length, protruding less than 0.5 mm beyond perianth; in cross-section, rectangular, about 1.3 mm by 0.8 mm. Stamens: Does not protrude beyong perianth; flat; firmly pressed against pistil; about 1.2 by 0.7 mm in size. Pollen not observed.

*Spathe.*—Length: About 5.3 cm. Width: About 4.1 cm. Length to width ratio: About 1.3 to 1. Shape: Ovate. Apex: Acuminate with aristate tendencies. Base: Cordate. Margin: Entire. Texture: Mostly smooth; almost flat with slight puckering near spadix base; glossy. Aspect: Horizontal to slightly upright; almost flat. Color: Closed bud (before unrolling): Close to 59C to 59D with narrow darker margin, between 187A to 187B and 59A. Newly unrolled spathe, front surface: 58A or slightly darker with narrow darker margin, 59A or darker. Mature spathe, front surface: 58A or lighter with narrow darker margin, 59A or darker. Mature spathe, back surface: Paler than 59D with narrow darker margin, between 183B, 187B and 59A.

*Spadix.*—Length: About 2.9 cm. Diameter: About 5.8 mm. Shape: Columnar, tapering at apex; mostly straight. Cross section: Rounded. Aspect: About 50 to 70° to spathe. Color: Young: Closest to 145C, but may resemble any of the following colors: 150C, 145D or 1C. Slight purple undertones in the proximal zone. Apex, 1C or 150C. Mature, proximal zone: Closest to 36B to 36D; pistils, 36D or lighter, almost white. Mature, intermediate zone: Closest to 77C to 77D, 78D and 87D. Mature, distal zone: Color not present in R.H.S. Colour Chart, but closest to between 145C and 195B to 195C. Mature, apex: 1C. With subsequent development, proximal zone becomes larger and more orange, paler and lighter than 31D, with stronger contrasting pistils. Intermediate zone becomes darker lavender and the distal zone becomes smaller and flushed with the color of intermediate zone and eventually becomes that color.

*Peduncle.*—Length: About 13.9 cm. Diameter: About 3 mm. Stipe length: About 2.3 mm. Aspect: Moderately strong; occasionally slightly bent; mostly vertical or angled outward slightly. Color: At junction with spathe: Front surface, 144A; back surface, 146B. Base: Slightly darker than 146A.

Disease/insect resistance: Plants of the new Anthurium have not been shown to be unusually susceptible to pathogens and insects common to Anthurium.

Seed development: Seed development on plants of the new Anthurium has not been observed.

It is claimed:

1. A new and ditinct cultivar of Anthurium plant named 'Aeighteen', as illustrated and described.

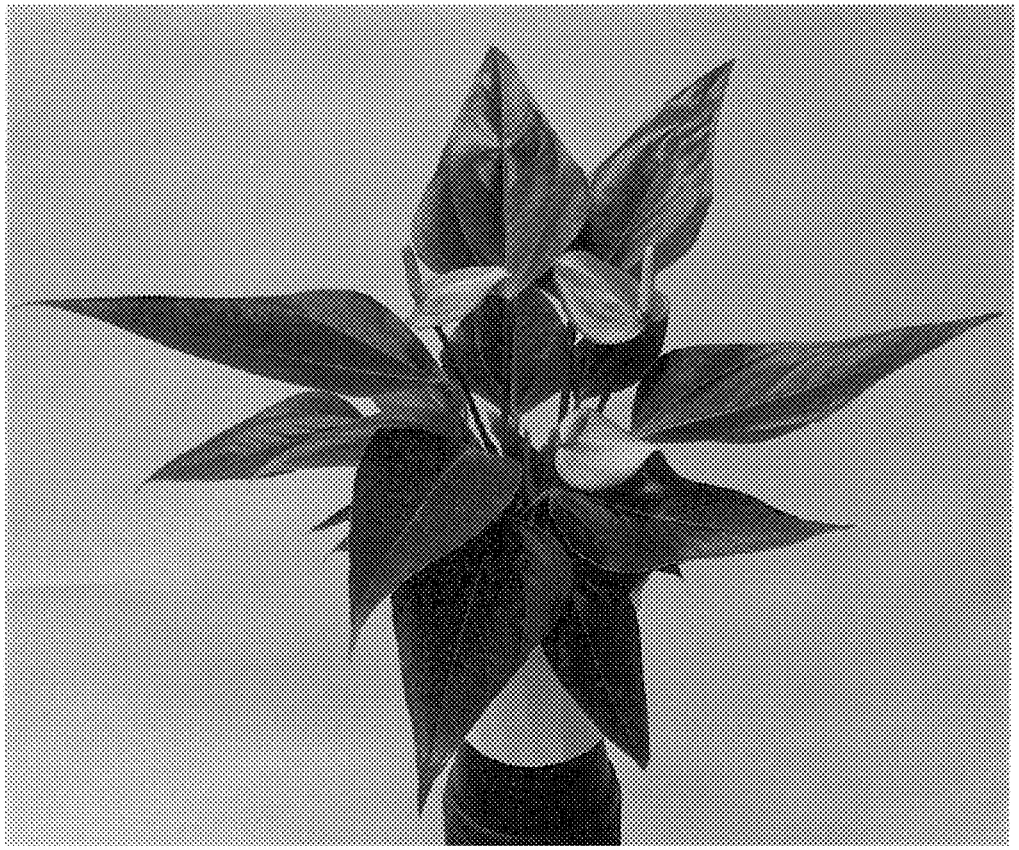
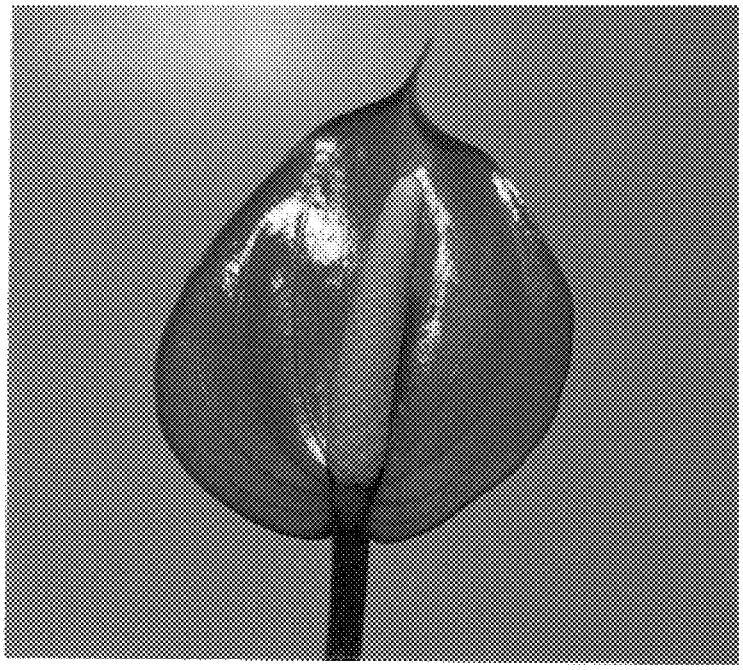

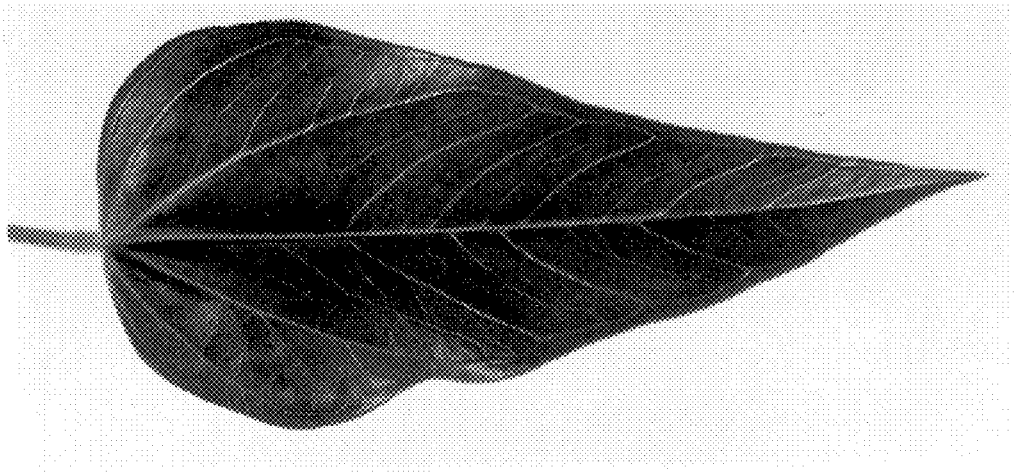
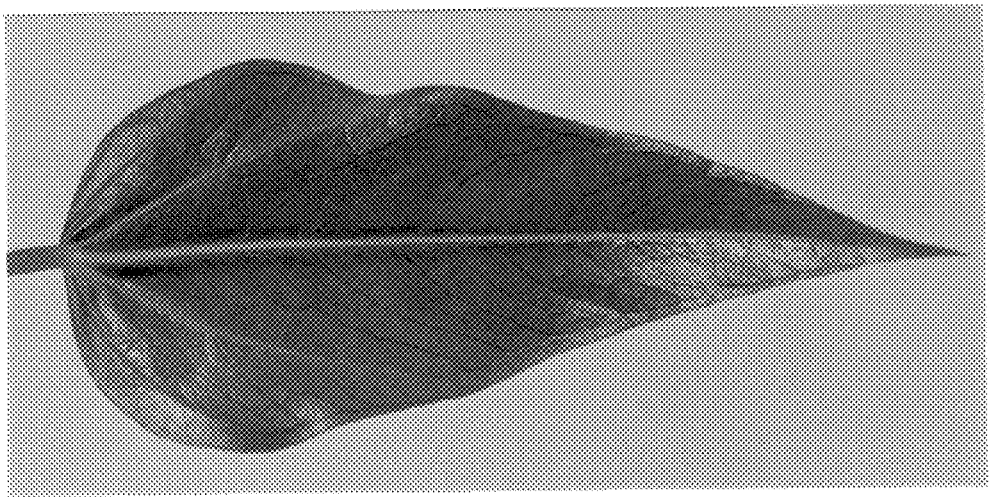

* * * * *